US012676237B2

(12) United States Patent
Dominick et al.

(10) Patent No.: US 12,676,237 B2
(45) Date of Patent: Jul. 7, 2026

(54) SYSTEM AND METHOD FOR PROVIDING AN ANALYTICAL RESULT BASED ON A MEDICAL DATA SET USING ML ALGORITHMS

(71) Applicant: Siemens Healthineers AG, Forchheim (DE)

(72) Inventors: Lutz Dominick, Eggolsheim (DE); Vladyslav Ukis, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 262 days.

(21) Appl. No.: 18/519,507

(22) Filed: Nov. 27, 2023

(65) Prior Publication Data

US 2024/0203591 A1      Jun. 20, 2024

(30) Foreign Application Priority Data

Dec. 14, 2022    (DE) ..................... 10 2022 213 653.5

(51) Int. Cl.
*G16H 50/20*        (2018.01)
*G06T 7/00*        (2017.01)
(Continued)

(52) U.S. Cl.
CPC ........... *G16H 50/20* (2018.01); *G06T 7/0012* (2013.01); *G06T 7/10* (2017.01); *G16H 30/40* (2018.01);
(Continued)

(58) Field of Classification Search
CPC . G06T 1/20; G06T 1/60; G16H 30/40; G16H 50/20; G16H 50/30; G16H 10/60;
(Continued)

(56) References Cited

U.S. PATENT DOCUMENTS 10,163,028 B2 * 12/2018 Rubens ................. G16H 30/20
11,120,299 B2    9/2021 Haigh et al.
(Continued)

FOREIGN PATENT DOCUMENTS

DE        102020209696 A1      2/2022
EP             3798934 A1      3/2021
WO      WO 2017129573 A1      8/2017

OTHER PUBLICATIONS

B. Nithya et al. , "Predictive Analytics in Health Care Using Machine Learning Tools and Techniques," Jan. 11, 2018, International Conference on Intelligent Computing and Control Systems, ICICCS 2017, pp. 492-499.*
(Continued)

*Primary Examiner* — Omar S Ismail
(74) *Attorney, Agent, or Firm* — Harness, Dickey & Pierce, P.L.C.

(57) ABSTRACT

Methods and systems for providing an analytical result by automated evaluation of a medical data set in a distributed runtime environment are provided. In response to a request to provide the analytical result from a client computing device, a suitable version of an ML algorithm is selected from an algorithm repository unit and applied in a back-end computing device. Selection is made on the basis of areas of application which, for each version in the algorithm repository unit, characterize the version.

16 Claims, 4 Drawing Sheets

(51) Int. Cl.
G06T 7/10 (2017.01)
G16H 30/40 (2018.01)

(52) U.S. Cl.
CPC .............. *G06T 2207/20081* (2013.01); *G06T 2207/20084* (2013.01); *G06T 2207/20112* (2013.01)

(58) Field of Classification Search
CPC ........ G16H 10/65; G16H 30/20; G16H 40/20; G16H 40/40; G16H 40/60; G16H 40/63; G16H 40/67
See application file for complete search history.

(56) References Cited

U.S. PATENT DOCUMENTS

| | | | | |
|---|---|---|---|---|
| 12,340,293 B2 * | 6/2025 | Gur | ........................... | G06F 8/36 |
| 2012/0189180 A1 * | 7/2012 | Yeluri | ................... | G16H 30/40 |
| | | | | 382/128 |
| 2017/0213101 A1 * | 7/2017 | Rubens | .................. | G16H 30/20 |
| 2019/0088359 A1 * | 3/2019 | Moore | .................. | G16H 30/20 |
| 2019/0180882 A1 * | 6/2019 | Han | ......................... | G06N 3/08 |
| 2019/0385711 A1 * | 12/2019 | Shriberg | ............... | G16H 15/00 |
| 2021/0019665 A1 * | 1/2021 | Gur | ......................... | G06N 20/20 |
| 2021/0097439 A1 * | 4/2021 | Vodencarevic | .......... | G06F 8/71 |
| 2021/0110895 A1 * | 4/2021 | Shriberg | ............... | G16H 10/20 |
| 2021/0224585 A1 | 7/2021 | Schmidt et al. | | |
| 2021/0398677 A1 * | 12/2021 | Lanius | ................ | G06N 3/0442 |
| 2022/0051049 A1 | 2/2022 | Wang et al. | | |
| 2022/0059221 A1 * | 2/2022 | Zhu | ...................... | G06V 10/806 |
| 2022/0139530 A1 | 5/2022 | Kollada et al. | | |
| 2022/0382539 A1 | 12/2022 | Gumashta et al. | | |
| 2022/0392637 A1 * | 12/2022 | Kollada | ............... | G16H 50/30 |
| 2022/0415472 A1 * | 12/2022 | Hakala | .................. | G06N 3/092 |

OTHER PUBLICATIONS

P. Suresh Kumar et al. , "Performance Analysis of Machine Learning Algorithms on Diabetes Dataset using Big Data Analytics," Feb. 8, 2018, 2017 International Conference on Infocom Technologies and Unmanned Systems (ICTUS'2017), Dec. 18-20, 2017, ADET, Amity University Dubai, UAE, pp. 508-511.*

Khoa A. Tran et al., "Deep learning in cancer diagnosis, prognosis and treatment selection," Sep. 27, 2021, Genome Medicine, vol. 13,Article No. 152( 2021) , pp. 1-8.*

Jafar Abdollahi et al., "Deep Neural Network Based Ensemble learning Algorithms for the healthcare system (diagnosis of chronic diseases)," Mar. 15, 2021, Computer Science , Machine learning, arXiv:2103.08182, pp. 1-7.*

* cited by examiner

SYSTEM AND METHOD FOR PROVIDING AN ANALYTICAL RESULT BASED ON A MEDICAL DATA SET USING ML ALGORITHMS

CROSS-REFERENCE TO RELATED APPLICATION(S)

The present application claims priority under 35 U.S.C. § 119 to German Patent Application No. 10 2022 213 653.5, filed Dec. 14, 2022, the entire contents of which is incorporated herein by reference.

FIELD

One or more embodiments of the present invention relate to systems and methods for providing an analytical result by evaluating a medical data set using an ML algorithm. In particular, one or more embodiments of the present invention relate to providing and/or selecting ML algorithms or versions of ML algorithms which are adapted for different types of preprocessing of the medical data sets. In particular, one or more embodiments of the present invention relate to systems and methods for selecting and adjusting the settings of ML algorithms or versions of ML algorithms and associated types of preprocessing in distributed computer systems/environments, in particular for resource and SLO optimization.

BACKGROUND

Independent of the grammatical term usage, individuals with male, female or other gender identities are included within the term.

Numerous algorithms are available in computer-assisted medical investigation which can be applied to medical data in order to detect clinical findings or clinical anomalies in the data and bring them to the user's attention. One outstanding example is for example "CAD" (computer-aided detection) algorithms which can be configured to automatically recognize medical anomalies such as for instance lesions in medical image data, such as for instance thoracic CT scans. Such algorithms frequently make use of artificial intelligence which has been trained for the specific use case. The use case may here comprise the fundamental task (for instance detection of possible lung nodules in MR captures of the lung) or the nature, scope or status of the medical data set to be analyzed.

In modern systems, such algorithms are in some cases applied automatically. In this way, the user can automatically be provided with analytical results which can be used in the subsequent investigation workflow which may ultimately lead, for example, to a medical investigation report with one or more medical diagnoses. Advantageously, such a medical investigation report may be produced at least partially automatically on the basis of automatically produced analytical results.

In this context, the elevated resource requirements of an increasingly powerful execution environment and hardware are disadvantageous. Algorithms based on artificial intelligence (also: machine learning (ML) algorithms) are here frequently particularly resource-intensive. It is therefore frequently out of the question to host such algorithms on the user's terminal. While relocating the computing load to edge- or cloud-based execution environments may mitigate such difficulties, it cannot eliminate the root cause. In particular, peak loads in practical use during which numerous requests have to be processed take even powerful systems to their load limit. It should be borne in mind here that medical data sets may inherently be very extensive. For instance, even simple series of images comprise of the order of 50 MB, while digital pathology images may comprise up to 1 GB of data. This demands commensurate resources when loading and storing such data. In addition, access times are limited by the data transmission capacities of the underlying networks.

This rapidly leads to conflicts with product requirements in computer-assisted investigation. In order to comply with acceptable parameters (which are often guaranteed in service level agreements (SLA)) with regard to availability, latency or quality, computer systems often have to be designed such that they can handle conceivable peak loads. On the other hand, these solutions are actually over-dimensioned for other phases and thus inefficient. In addition, such systems can often only be scaled via hardware which complicates and increases the costs of possible expansion with regard to the offered algorithms (and thus use cases) and the number of simultaneously supported clients/users.

SUMMARY

It is an object of the embodiments of the present invention to provide systems and methods which enable improved and more efficient resource utilization in the provision of analytical results for medical data sets by ML algorithms.

These and further objects are achieved with methods, systems, computer program products or computer-readable storage media according to the main claim and the independent claims. Advantageous further developments are indicated in the dependent claims.

At least the aforementioned object is achieved according to the present invention as described below both in relation to the claimed systems and in relation to the claimed methods. Features, advantages or alternative embodiments/aspects mentioned in this connection are likewise also transferable to the other claimed subjects and vice versa. In other words, the substantive claims (e.g. directed to a system) can also be further developed with the features which are described or claimed in connection with a method. The corresponding functional features of the method may here be embodied by corresponding substantive modules.

Furthermore, the object achieved according to embodiments of the present invention is also described in relation to methods and systems for adapting trained functions. Features and alternative embodiments/aspects of data structures and/or functions in methods and apparatuses can be transferred in the application of a trained function to analogous data structures and/or functions in methods and systems for adaptation. Analogous data structures can here in particular be characterized by the use of the qualifier "training". Furthermore, the trained functions used in methods and apparatuses may in particular have been adapted and/or provided by methods and systems for adaptation of trained functions.

One aspect provides a system or a computing device for providing an analytical result based on an evaluation of a medical data set. The system or computing device has an interface, an algorithm repository unit and a processing unit. The interface is linked for data purposes to a second computing device and is configured to receive medical data sets and a request to provide an analytical result from the second computing device and to provide the analytical result to the second computing device. The algorithm repository unit contains (stores) at least one trained ML algorithm, which ML algorithm has been trained to provide a specific analytical result (or a predetermined kind of analytical result) on the basis of medical data sets, and, for each ML algorithm, a plurality of areas of application, each area of application of an ML algorithm corresponding to a different type of preprocessing of the medical data set prior to application of the ML algorithm. The processing unit is configured to select an ML algorithm from the algorithm repository unit on the basis of the request, to select an area of application for the selected ML algorithm on the basis of the request and/or the medical data set, to request preprocessing of the medical data set in accordance with the preprocessing associated with the selected area of application so as to provide a preprocessed data set, and to apply the ML algorithm to the preprocessed medical data set in order to provide the analytical result.

One aspect provides a method for providing an analytical result based on an evaluation of a medical data set in a medical network with a computing device and a second computing device. The method has a plurality of steps. One step is directed to receiving a request from the second computing device to provide an analytical result of the medical data set in the computing device. One step is directed to providing at least one trained ML algorithm in the computing device, which ML algorithm has been trained to provide analytical results on the basis of medical data sets. One step is directed to providing a plurality of areas of application of the at least one ML algorithm in the computing device, each area of application corresponding to a different type of preprocessing of the medical data set prior to application of the ML algorithm. One step is directed to the computing device selecting an area of application of the at least one ML algorithm on the basis of the request and/or the medical data set. One step is directed to the computing device requesting preprocessing of the medical data set in accordance with the preprocessing associated with the selected area of application so as to provide a preprocessed data set. One step is directed to the computing device applying the at least one ML algorithm to the preprocessed medical data set in order to provide the analytical result. One step is directed to the computing device providing the analytical result to the second computing device.

A further aspect of embodiments of the present invention relates to a computer program product which comprises a program and is directly loadable into a memory of a programmable controller and has program means, for example libraries and auxiliary functions, in order to carry out a method for providing an analytical result, in particular according to the embodiments/aspects stated herein, when the computer program product is executed.

A further aspect of embodiments of the present invention furthermore relates to a computer-readable storage medium on which readable and executable program parts are stored, in order to carry out all the steps of a method for providing an analytical result according to the embodiments/aspects stated herein, when the program parts are executed by the controller.

The computer program products may in this respect comprise software with source code which has yet to be compiled and linked or has merely to be interpreted, or executable software code which has merely to be loaded into the processing unit for execution. The methods can be carried out quickly, identically repeatably and robustly by the computer program products. The computer program products are configured such that they can carry out the method steps according to embodiments of the present invention by way of the computing unit. The computing unit must here in each case comprise the prerequisites such as for example an appropriate working memory, an appropriate processor, an appropriate graphics card or an appropriate logic unit for it to be possible to carry out the respective method steps efficiently.

The computer program products are for example stored on a computer-readable storage medium or saved on a network or server, from where they can be loaded into the processor of the respective computing unit, which processor may be directly connected to the computing unit or be configured as part of the computing unit. Control information of the computer program products may furthermore be stored on a computer-readable storage medium. The control information of the computer-readable storage medium may be configured such that, when the data storage medium is used in a computing unit, it carries out a method according to embodiments of the present invention. Examples of a computer-readable storage medium are a DVD, a magnetic tape, or a USB stick on which electronically readable control information, in particular software, is stored. If this control information is read from the data storage medium and stored in a computing unit, all the embodiments/aspects according to the present invention of the previously described methods can be carried out. The invention may accordingly also be based on said computer-readable medium and/or said computer-readable storage medium. The advantages of the proposed computer program products or of the associated computer-readable media substantially correspond to the advantages of the proposed systems or methods.

The computing device and the second computing device may be computing devices which are remote or physically separate from one another which may be linked for data purposes via a medical network (via the interface). The medical network (or medical information network) can be configured to exchange medical information, thus in particular medical data sets and requests to produce an analytical result and the like. The medical network can in particular establish a communication and/or data link between the second computing device and the computing device. The medical network can additionally establish a communication and/or data link with further medical data processing devices such as for instance repository devices for storing data. The medical network may comprise an intranet and/or the internet. In other words, the second computing device may have a communication and/or data link with the computing device via the internet. The request and/or the medical data set may furthermore be provided to the computing device via the internet (by the second computing device). Conversely, the medical report can be transmitted (by the computing device) to the second computing device via the internet.

According to some embodiments, communication or data links may be based on the HL7 standard. Health level 7 (HL7) is a group of international standards for the exchange of data between healthcare organizations and their computer systems. In particular, communication and/or data links may be based on the FHIR standard. Fast Healthcare Interoperability Resources (FHIR) is a standard drawn up by HL7 which supports data exchange between healthcare software systems. Using the HL7 or FHIR standard allows data to be transmitted in structured form without reformatting being necessary.

The second computing device (also denoted client computing device or client, or front-end computing device) may in particular be configured as an investigation workstation or investigation station on which a user (in particular a member of medical personnel such as a physician) can retrieve and/or view and/or analyze patient data, and/or on which the user can retrieve and/or view and/or modify medical reports and/or on which the user can request and/or view analytical results. The second computing device may to this end have a user interface. The second computing device may for example be configured as a desktop PC, laptop, tablet, smartphone or the like or comprise the stated components.

The interface may in general be configured for data exchange between the computing device and further components, in particular the second computing device and furthermore in particular via the medical network. The interface may be implemented in the form of one or more individual data interfaces which may have a hardware and/or software interface, for example a PCI bus, a USB interface, a FireWire interface, a ZigBee or a Bluetooth interface. The interface may furthermore be a communication network interface, the communication network possibly including a local area network (LAN), for example an intranet or a wide area network (WAN), or the internet. Accordingly, the one or more data interfaces may have a LAN interface or a wireless LAN interface (WLAN or WiFi). In particular, the interface may be based on the HL7 or FHIR standard.

The algorithm repository unit may be configured as a centralized or distributed repository unit or cloud storage system. The algorithm repository unit may in particular be configured as part of the computing device.

The computing device (also denoted back-end computing device or server computing device) may also be configured as a server system. The computing device may include a cluster or a group of computing devices and data storage media. The computing device may not have a user interface for the user (of the second computing device). The computing device may be linked for data purposes to the second computing device via the medical network. The computing device may be linked for data purposes to a plurality of other (but in particular similar) second computing devices via the medical network. The second computing device(s) may belong to a medical organization, such as for instance a clinic, a hospital or a hospital group. The computing device may likewise belong to the medical organization or be located outside the medical organization. The computing device may be linked for data purposes via the medical network with a plurality of other second computing devices which in each case belong to different medical organizations.

The computing device may have one or more virtual or real computing nodes or machines. In particular, the computing device may be configured as a Kubernetes-based system in which the computing nodes are configured as Kubernetes nodes.

The computing device may in particular have a processing unit. The processing unit may have a control module for sequential control and one or more computing modules for performing the processing, such as for instance the preprocessing or application of the ML algorithm. The control module (also denoted control node) may be configured to select an ML algorithm from the algorithm repository unit on the basis of the request, to select an area of application for the selected ML algorithm on the basis of the request and/or the medical data set, and to request preprocessing of the medical data set in accordance with the preprocessing associated with the selected area of application so as to provide a preprocessed data set. The control module may furthermore be configured to request resources for application of ML algorithms or allocate them in the back-end computing device. These resources may for example comprise a computing module. According to some embodiments, the control module may be configured as a virtual machine or server. According to some embodiments, the control module may be configured as a Kubernetes-based "master node" or control node.

The one or more computing modules (also denoted computing nodes) may likewise be configured as virtual machines or servers and/or according to some embodiments be configured as Kubernetes-based worker nodes (or "minion nodes"). The one or more computing modules may be configured to host "pods" in which the actual calculation of the analytical results takes place.

The medical data set may be associated with a patient. The medical data set may comprise both medical image data and non-image data. In this context, image data may relate to medical image data with two or three spatial dimensions. The image data may additionally have a temporal dimension. Medical image data are here in particular image data which have been captured with an imaging modality and may in particular represent a body part of the patient. Imaging modalities may for example comprise computed tomography devices, magnetic resonance imagers, X-ray machines, ultrasound scanners and the like. Image data captured using such or similar modalities is also denoted radiology image data. Medical image data may furthermore comprise digitized histopathology images which represent an appropriately dissected tissue section from a patient. The image data may furthermore comprise longitudinal data, for instance in the form of time series or temporally spaced follow-up captures. The image data may for example be formatted in DICOM format. DICOM here denotes digital imaging and communications in medicine and denotes an open standard for storing and exchanging information in medical image data management.

Non-image data may comprise in particular longitudinal data which contains one or more patient medical values and/or elements from the patient's disease history. Such data may comprise laboratory data, vital values and/or other measured values or prior investigations relating to the patient. The non-image data may furthermore comprise demographic details relating to the patient, for instance relating to age, gender, lifestyle, risk factors etc.

The medical data may here be retrieved, in particular by the front-end computing device, from one or more repository devices which may be integrated in the medical information network or be linked for data purposes to the second computing device. The user may, for example, select an investigation task or a patient from a worklist in a second computing device. On the basis of the selected investigation task or patient, the connected repository devices can be queried for the patient's data. An electronic identifier, such as for instance a patient ID or an accession number, may for example be used for this purpose. The medical data may accordingly be received from one or more of the available repository devices in which in each case at least parts of the medical data set are stored. The repository devices may here for example be part of medical information systems, such as for instance hospital information systems and/or PACS systems and/or laboratory information systems etc.

An ML algorithm generally maps input data onto output data. The output data may here in particular depend on one or more parameters of the ML algorithm. Other terms for ML algorithm are trained function, trained mapping rule, mapping rule with trained parameters, function with trained parameters, algorithm based on artificial intelligence or machine learning algorithm etc.

One example of an ML algorithm is an artificial neural network. The term "neural net" can also be used instead of the term "neural network". A neural network is fundamentally of the same structure as a biological neural network, for instance a human brain. An artificial neural network in particular comprises an input layer and an output layer. It may furthermore comprise a plurality of layers between input and output layers. Each layer comprises at least one, preferably a plurality of, nodes. Each node can be understood as a biological processing unit, for example as a neuron. In other words, each neuron corresponds to an operation which is applied to input data. Nodes of one layer can be connected by edges or connections to nodes of other layers, in particular by directional edges or connections. These edges or connections define the flow of data between the nodes of the network. The edges or connections are associated with a parameter which is frequently denoted "weight" or "edge weight". This parameter can regulate the importance of the output of a first node to the input of a second node, the first and second nodes being connected by an edge. A trained function may in particular also have a deep artificial neural network (also "deep neural network").

According to one aspect, the ML algorithm has a convolutional neural network and in particular a domain-based convolutional neural network.

The convolutional neural network may in particular be configured as a deep convolutional neural network. The neural network here has one or more convolutional layers and one or more deconvolutional layers. In particular, the neural network may comprise a pooling layer. Using convolutional layers and/or deconvolutional layers allows a neural network to be deployed particularly efficiently for image processing since, despite numerous connections between node layers, only few edge weights (namely the edge weights corresponding to the values of the convolutional kernel) have to be determined. Using an identical volume of training data, the accuracy of the neural network can thus also be improved.

According to further embodiments, the ML algorithm comprises a support vector machine, a k-next-neighbor algorithm, a decision tree algorithm, and/or a naive Bayes algorithm.

An ML algorithm learns by adapting parameters which determine the mapping of input data onto output data. In neural networks, these parameters are for example the weights or weighting parameters (e.g. the edge weights) of individual layers and nodes. A trained function may for example be trained by supervised learning methods. The backpropagation method may be used here, for example. During training, the ML algorithm is applied to training input data in order to produce corresponding output values, the target values of which are known in the form of training output data. The difference between the output values and the training output data can be used to introduce a cost or loss functional as a measure of how well or poorly the ML algorithm is achieving its set task. The goal of training is to find a (local) minimum of the cost functional by iteratively adapting the parameters (e.g. the edge weights) of the ML algorithm. As a result, the ML algorithm is enabled to provide acceptable results over a (sufficiently) large cohort of training input data. This optimization problem can be addressed by using a "stochastic gradient descent" method or other approaches known in the art.

According to some embodiments, training data sets would in each case include medical training data sets and associated verified analytical results. The verified analytical results could here be based on annotation by a user who has provided this on the basis of an analysis or investigation of the medical training data set.

According to some embodiments, training of the ML algorithm could thus then comprise applying the ML algorithm to the medical training data sets to produce output values and comparing the output values with verified analytical results. One or more parameters of the ML algorithm can then be adapted on the basis of the comparison.

An analytical result can relate to an item of information in the medical data set. An analytical result may be indicative of a specific state or a specific disease process of the patient to be investigated. The state or disease process may be of relevance to the diagnosis of the patient to be investigated.

An analytical result may relate to a structure or an item of data which differentiates the patient from other (healthy) patients. Analytical results may relate to various organs or anatomical features of the patient (e.g. the lungs or liver or skeletal structure).

In particular, an analytical result may relate to structures or patterns shown in medical image data of the medical data set. In particular, a medical anomaly underlying an analytical result may relate to a neoplasm (also denoted "tumor"), in particular a benign neoplasm, an in situ neoplasm, a malignant neoplasm and/or a neoplasm with uncertain/unknown behavior. In particular, an analytical result may relate to a nodule, in particular a lung nodule. In particular, an analytical result may relate to a lesion, in particular a lung lesion. The analytical result may furthermore relate to one or more tumor cells in histopathology image data.

An analytical result may furthermore relate to an anomalous data value or a combination of anomalous data values in the medical data set. For example, an analytical result may relate to a laboratory value which deviates from a standard, such as for instance a PSA value or vital values.

A request may be taken to be an order to the computing device to provide a specific analytical result on the basis of a specific medical data set. The request may be produced automatically by the second computing device or be input by a user of the second computing device.

The request may accordingly comprise an item of execution information. The execution information may for example define what kind of analysis is to be carried out. The execution information may furthermore define which kind of ML algorithms is to be applied to the medical data set. The request may furthermore comprise a timeframe for the provision of the analytical result. The request may furthermore comprise a quality criterion which must be met by the analytical result. The quality of the analytical result may for example be expressed by the confidence/confidence value, specificity, sensitivity, and/or signal-noise ratio etc. of the analytical result.

The area of application may be taken to be that range of parameters for which the respective ML algorithm or a version of the ML algorithm has been trained. The area of application may here in particular indicate the resources which are to be used in the computing device on application of the ML algorithm (or the associated version of the ML algorithm). The area of application may furthermore indicate the achievable quality (given the specific preprocessing). Various areas of application are obtained by different types of preprocessing which are to be applied to a medical data set before it can be input into the ML algorithm.

Different types of preprocessing here result in different resource requirements and can lead to a different quality or grade of the analytical results. Extensive preprocessing may accordingly result in improved quality but will (at least during execution of the preprocessing) require greater computing resources. Conversely, extensive preprocessing may result in lower resource requirements on application of the ML algorithm. If, for example, a specific and computationally costly organ segmenter is used as preprocessing upstream of a CAD algorithm for identifying lesions in a specific organ, an improved quality level may be obtained with lower computational effort on application of the CAD algorithm. The computing device can establish which strategy or which area of application is suitable for the particular situation for example by solving an optimization problem.

According to some examples, the different types of preprocessing may in each case give rise to different levels of computational effort on application of the ML algorithm and/or different levels of quality of the analytical result. Furthermore, the different types of preprocessing may themselves require different levels of computational effort.

Preprocessing may in general be a data processing step which adjusts the medical data set into a form suitable for application of the respective ML algorithm. Preprocessing may here comprise minimizing or filtering data, which according to some examples may involve extracting elements or parts of the medical data set from the latter. For example, individual items of information, for instance a time series of observables and/or specific image data (for instance of a specific organ) may be extracted in this way from the medical data set. Preprocessing may furthermore comprise conversion of the medical data set or of parts thereof into another format. Preprocessing may furthermore comprise improving the medical data set or parts thereof. This may for example comprise improving a signal-to-noise ratio or contrast.

By the provision of various areas of application with associated types of preprocessing, it is possible to select suitable areas of application dynamically in order to meet a request. As a result, resources can be better managed in the computing device. This enables more efficient resource utilization in the provision of analytical results for medical data sets. A further improvement in efficiency may furthermore be achieved by separation of the preprocessing since the latter may optionally be outsourced for better resource utilization.

According to one aspect, the algorithm repository unit furthermore comprises a different version of the ML algorithm for each area of application of the ML algorithm, which versions are specific to the respective area of application (and provide the same predetermined kind of analytical result), the control module is furthermore configured to select the version of the ML algorithm which corresponds to the selected area of application, and the computing node is configured, on application of the ML algorithm, to apply the selected version of the ML algorithm to the preprocessed medical data set in order to provide the analytical result.

In particular, the versions may be taken to be different implementations of one and the same ML algorithm. In particular, on application to a medical data set, the versions of the ML algorithm may at least provide the same analytical result per type (e.g. an indication of one or more lesions in the lung). According to some examples, the different versions of an ML algorithm may, however, in each case give rise to different levels of computational effort on application of the ML algorithm and/or different levels of quality of the analytical result. Quality may, for example, comprise a sensitivity and/or specificity and/or confidence and/or signal-to-noise ratio of the analytical result.

According to one aspect, the version of the ML algorithm associated with a specific area of application corresponds to a version (or instance) of the ML algorithm which has been trained on the basis of data which were preprocessed with the preprocessing associated with the area of application.

The provision of different versions makes it possible to provide "variants" of one and the same underlying ML algorithm which have been optimized for the particular type of preprocessing. Efficient resource utilization can thus be achieved.

According to one aspect, the areas of application in each case contain performance characteristics of the ML algorithm during the respective preprocessing, and the processing unit (the control module) is configured to select the area of application additionally on the basis of the performance characteristics.

According to one aspect, the areas of application may in each case include performance characteristics of the corresponding version of the ML algorithm during the respective preprocessing.

Provision of the performance data makes it possible to select the specific area of application or specific version of the ML algorithm which is most appropriate for the circumstances. This enables efficient resource utilization.

According to one aspect, the performance characteristics state an item of information characterizing the quality of a corresponding analytical result and an item of information characterizing the consumption of resources on application of the selected ML algorithm.

According to one aspect, the performance characteristics include an item of information characterizing the quality of a corresponding analytical result and/or the consumption of resources on application of the corresponding version of the selected ML algorithm for the respective preprocessing and/or the consumption of resources on application of the corresponding preprocessing.

Knowledge of the quality and resource consumption of an area of application/version makes it possible to achieve a balance between these quantities. For instance, in the event of a high level of utilization, it is possible to select an area of application which yields analytical results which are still acceptable in quality terms while requiring sufficiently low computational effort.

According to one aspect, the processing unit is furthermore configured to establish, in particular on the basis of the request and/or information saved in the computing device relating to the second computing device, at least one performance limit value which must be complied with on provision of the analytical result, and to select the area of application additionally on the basis of the performance limit value and in particular on the basis of a comparison between the performance limit value and the performance characteristics.

A performance limit value may for example be defined directly or indirectly on the basis of an agreement between the organizations to which the second computing device and the computing device belong. Such an agreement is also denoted a service level agreement (SLA). Such an agreement may in particular be saved in the computing device and queried in response to a request. Individual performance limit values may also be considered to be clearly measurable service level objectives (SLOs) which must be complied with if the SLA is to be fulfilled. Alternatively, a performance limit value may be transmitted together with the request or be present therein. As a further alternative, a performance limit value may also be predetermined for an ML algorithm or a kind of analytical result (thus in particular predetermined independently of the request or the front-end computing device).

Performance limit values may for example comprise a maximum tolerable time for the provision of the analytical result and/or a minimum quality of the analytical result.

Taking the performance limit values into account allows the areas of application to be selected in a manner appropriate to the circumstances and thus efficient resource utilization.

According to one aspect, the processing unit may furthermore be configured to apply a buffer value to the at least one performance limit value and to select the area of application additionally on the basis of the performance limit value to which the buffer value has been applied and in particular on the basis of a comparison between the performance limit value to which the buffer value has been applied and performance characteristics. Compliance with the performance limit value can be ensured in this way.

In particular, working ranges may thus be selected such that system parameters (such as for instance the quality of an analytical result or the provision time and/or the consumption of resources on provision of the analytical result) run within a target corridor which complies with the service level agreement (SLA). The system parameters selected in this way may also be understood as a service level objective (SLO). The performance limit values (to which the buffer values have optionally been applied) are thus clearly measurable parameters, compliance with which ensures that the SLA is complied with.

According to one aspect, the processing unit is configured to select the area of application on the basis of the performance characteristics in such a manner as to optimize the quality of the analytical result to be provided and/or the consumption of resources for provision of the analytical result.

In particular, the processing unit may be configured to select the area of application on the basis of an evaluation of a cost function.

For example, the processing unit may be configured to evaluate (in particular minimize) an optimization function or cost functional on the basis of the performance characteristics for each area of application so as to compare various areas of application and select an area of application in such a manner as to optimize the quality of the analytical result to be provided and/or the consumption of resources for provision of the analytical result.

For example, the cost functional may be configured such that the performance characteristics and/or performance limit values can be input (or taken into account) in the cost functional.

Optimization with regard to quality and/or consumption of resources makes it possible to identify an appropriate area of application and thus an appropriate version of the ML algorithm. As a result, available resources can be efficiently utilized.

According to one aspect, the processing unit is furthermore configured to acquire an item of status information of the computing device and/or of the second computing device and/or of a data transmission between the computing device and the client computing device and to select the area of application additionally on the basis of the status information.

For example, the status information may comprise information about a level of utilization of computing resources of the computing device and/or the second computing device and/or of data transmission capacities of a data transmission between the computing device and the second computing device.

According to one aspect, the processing unit is configured to select the area of application on the basis of the performance characteristics and the status information in such a manner as to optimize the quality of the analytical result to be provided and/or the consumption of resources for provision of the analytical result.

For example, the cost function may be configured such that the status information may (additionally) be input into the cost function (or taken into account therein).

Taking the status information into account makes it possible to estimate how many resources are available overall for provision of the analytical result. On this basis, an area of application appropriate to the system status can be determined. For example, at a high level of system utilization, reductions in quality may for example be accepted and resource-saving preprocessing (and an associated version of the ML algorithm) selected.

According to one aspect, the processing unit is configured to determine on the basis of the status information and/or the selected area of application and/or the performance characteristics whether the preprocessed data set (the preprocessing) is to be requested from the second computing device or a resource within the computing device, and to request the preprocessed data set as a function of the determination from the second computing device or from the resource within the computing device.

In this way, it is possible to define dynamically where preprocessing is to proceed. It is thus possible to respond flexibly to any peak loads in the computing device.

According to one aspect, the processing unit is configured to request the preprocessed medical data set from the second computing device and optionally to provide the second computing device with a means, mechanism and/or functionality for providing the preprocessed data set.

The means, mechanism and/or functionality for providing the preprocessed data set may for example comprise algorithms or computer program products which are suitable for performing preprocessing of the medical data set appropriate to the area of application in a computing device.

Preprocessing in the second computing device may on the one hand relieve the load on the computing device. On the other hand, preprocessing can identify those parts of the medical data set which are of relevance to the calculation of the analytical result. As a result, the volume of data to be transmitted can be minimized so in turn saving data transmission capacity between the computing devices.

According to one aspect, the ML algorithms have in each case been trained by carrying out in each case at least one training step using the various types of preprocessing corresponding to the areas of application.

According to one aspect, the version of an ML algorithm corresponding to an area of application is provided by the ML algorithm having been adapted (trained) on the basis of a training step using the preprocessing corresponding to the area of application.

In other words, a version of an ML algorithm corresponds to an instance or implementation of the ML algorithm which has been adapted (trained) using appropriate preprocessing.

In other words, ML algorithms are provided which are adapted for use of the respective preprocessing. As a result, resources can be more efficiently utilized and, generally speaking, better analytical results are provided. The various versions of an ML algorithm corresponding to the various types of preprocessing may be understood as a kind of "library" of different implementations which have be specifically optimized for the respective preprocessing/area of application.

According to one aspect, the medical image data set comprises medical image data, the analytical result is based on detection of medical anomalies in the medical image data, and the preprocessing comprises preprocessing of the medical image data, in particular segmentation of the medical image data.

The described advantages are particularly apparent on application to medical image data. This is because the processing of medical image data is regularly particularly computationally intensive and suitable preprocessing can have a positive impact on the analytical result.

According to one aspect, the medical image data represents an anatomical region of the patient and segmentation is configured to segment at least one organ of the anatomical region. According to one aspect, the analytical result relates to the at least one segmented organ. According to a further aspect, the medical image data is a stained tissue section from the patient and segmentation is configured to segment at least one tissue type. According to one aspect, the analytical result relates to the at least one segmented tissue type.

According to one aspect, the medical image data has been produced on the basis of an imaging protocol, an imaging protocol being associated with each area of application, and the processing unit being configured to acquire the imaging protocol of the medical image data and to select the area of application additionally on the basis of the acquired imaging protocol and the associated imaging protocol.

According to one aspect, the processing unit is configured to detect the imaging protocol on the basis of the medical image data and in particular on the basis of an analysis of the medical image data and/or on the basis of metadata associated with the medical image data.

For example, an imaging protocol may indicate a modality with which the medical image data was captured. Additionally or alternatively, an imaging protocol can indicate one or more imaging parameters with which a modality for capturing the medical image data was actuated. Additionally or alternatively, an imaging protocol may indicate one or more image reconstruction parameters which were used for producing the medical image data set on the basis of raw data.

The image reconstruction parameters may relate to the reconstruction algorithm and the corresponding settings which are used for processing the acquired raw data in order to provide the medical image data set. Taking the CT imaging process by way of example, an image reconstruction parameter can specify the kernel (or convolution algorithm) used. The kernel refers to the process which is used to modify the frequency content of the projection data prior to backprojection during image reconstruction in a CT scanner. This process corrects the image by reducing blur. Various kernels have been developed for specific anatomical applications, for example for soft tissue (standard kernel) or bone (bone kernel).

Taking account of imaging protocols during identification of the areas of application is advantageous because application of the ML algorithm can in this way be coordinated with the area of application. Improved analytical results can in this way be achieved with identical consumption of resources.

According to one aspect, the computing device furthermore comprises a training computing device which is configured to carry out an evaluation of the analytical result provided by the processing unit and, on the basis of the analytical result, to adapt the area of application and/or the ML algorithm, in particular by way of further training of the ML algorithm.

According to one aspect, adaptation/further training of the ML algorithm comprises producing a new version of the ML algorithm and an associated area of application.

The training computing device may, for example, be configured to carry out an evaluation on the basis of a user input relating to the analytical result. Alternatively, the training module may be configured to carry out an automatic evaluation of the analytical result.

The available ML algorithms or areas of application can be further improved by the training module. In particular, the "library" of available areas of application and associated versions of the ML algorithm can be expanded in this way.

According to one aspect, the computing device is at least in part configured as an edge and/or cloud device.

According to one aspect, the computing device is configured as a Kubernetes-based system. In particular, the processing unit may be configured as or include one or more Kubernetes nodes. In particular, the control module may be configured as or include a Kubernetes master node. In particular, computing modules make be configured as or include Kubernetes worker nodes.

The design as an edge or cloud device or as a Kubernetes-based system means that computing resources can be dynamically allocated and for example need not be provided by the operator of the second computing device.

One aspect provides a method for providing an algorithm repository unit (ALG-REP). The method has a plurality of steps. One step is directed toward providing an ML algorithm which is configured to provide an analytical result on the basis of a medical data set (or on the basis of processing of a medical data set). One step is directed toward providing a medical training data set and an associated verified analytical result. One step is directed toward applying preprocessing to the medical training data set to produce a preprocessed training data set. One step is directed toward applying the ML algorithm to the preprocessed training data set to produce an intermediate analytical result. One step is directed toward comparing the intermediate analytical result with the verified analytical result. One step is directed toward adapting the ML algorithm on the basis of the comparison. One step is directed toward creating an area of application of the ML algorithm on the basis of the comparison, the area of application including an indication of the applied preprocessing. One step is directed toward storing the adapted ML algorithm and the area of application in the repository unit.

The medical training data set may have characteristics which are identical or at least similar to those of the medical data set. In particular, the medical training data set may have components identical or similar to those of the medical data set. The verified analytical result may for example be verified or provided by a human expert on the basis of the medical training data set.

Provision of the repository unit means that a library of areas of application which are defined for various types of preprocessing and thus system statuses can be established. This achieves a prerequisite for the flexible allocation of types of preprocessing, so enabling more efficient resource utilization.

According to one aspect, the adapted ML algorithm is stored in the repository unit as the version of the ML algorithm associated with the area of application.

According to one aspect, the method furthermore comprises a step of logging performance characteristics of the adapted ML algorithm (or version of the ML algorithm) during the applied preprocessing, and a step of including the performance characteristics in the area of application.

Logging the performance characteristics during training is a simple way of providing these values for further use.

According to one aspect, the method furthermore comprises a step of verifying whether the area of application constitutes an improvement in performance (in particular on the basis of the logged performance characteristics and furthermore in particular in comparison with the versions of the ML algorithm stored in the algorithm repository unit), the area of application or the adapted ML algorithm only being stored in the algorithm repository unit in the event of a performance improvement being identified on the basis of the verification step.

BRIEF DESCRIPTION OF THE DRAWINGS

Further specific features and advantages of the present invention are revealed by the following explanations of exemplary embodiments with the assistance of schematic drawings. Modifications stated in this connection may in each case be combined with one another in order to provide new embodiments. Identical reference signs are used for identical features in different figures.

In the figures.

DETAILED DESCRIPTION

Figure 1:
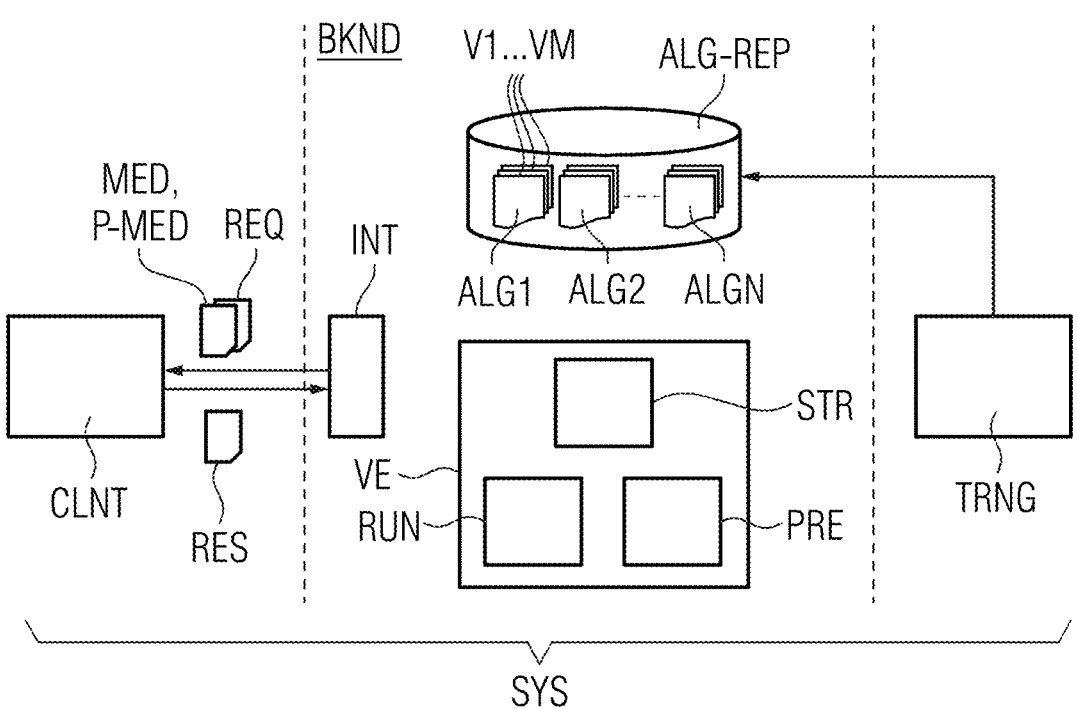
FIG. 1 shows a schematic representation of an embodiment of a system for providing an analytical result.

FIG. 1 shows a system SYS for providing an analytical result RES according to one embodiment. The system SYS has at least one front-end computing device CLNT (or "client" or "second computing device"), a back-end computing device BKND (or "server" or "computing device") and, optionally, a training computing device TRNG. The system SYS is generally configured to provide a user at the front-end computing device CLNT with an analytical result RES by automatically evaluating a medical data set MED. In order to evaluate the medical data set MED, the system SYS is configured to select an ML algorithm ALG1 . . . ALGN and apply it to the medical data set MED or a suitably preprocessed medical data set P-MED. The ML algorithms used are in turn configured to process medical data sets MED, P-MED as input data and to provide a corresponding analytical result RES as output data. The request to produce an analytical result RES may be provided by the front-end computing device CLNT in the form of a corresponding request REQ.

In the example shown in FIG. 1, the back-end computing device BKND has one or more interfaces INT, an algorithm repository device ALG-REP and a processing unit VE.

The individual components of the system SYS can be linked for data purposes with one another via a network, such as for instance the internet or an intranet. Medical data sets MED, P-MED, analytical results RES, requests REQ and further information can be exchanged between the front-end computing device CLNT and the back-end computing devices BKND via suitable interfaces INT. A system SYS as shown in FIG. 1 typically has a plurality of front-end computing devices CLNT, all of which access the same back-end computing device BKND.

According to some embodiments, the back-end computing device BKND may be understood as a server system, such as for example, a local server or a cloud server. Communication between the front-end computing device CLNT and the back-end computing device BKND may then be performed for example on the basis of an https protocol. In such systems, computing power can be divided between the front end and back end. In a "thin client" system, the back end has the majority of the computing power, while in a "thick client" system it is the front end which provides more computing power. A similar situation applies to the data. While in the "thin client" system most of the data remains on the back end and only the results are transmitted to the front end, in the "thick client" system data is also transmitted to the front end.

According to further embodiments, the described functionality may also be provided as a "cloud" or "web" service. The correspondingly configured back-end computing unit is then configured as a cloud or web platform. The data to be analyzed, i.e. the medical data set MED together with the request REQ, can then be uploaded onto this platform (e.g. via a suitable web interface).

The front-end computing device CLNT may for example be configured as an investigation station or investigation workstation on which a user can view and analyze patient data or a medical data set MED, and review, modify and appraise analytical results RES. The front-end computing device CLNT may to this end have a user interface comprising a display and/or an input device. The front-end computing device CLNT may have a processor. The processor may have a central processing unit (CPU), a graphics processing unit (GPU), a digital signal processor (DSP), an image processing processor, an integrated (digital or analog) circuit or combinations of the above-stated components and further devices. The front-end computing device CLNT may for example comprise a desktop PC, a laptop, a smartphone, a tablet or the like.

The front-end computing device CLNT may be linked for data purposes with a local medical information system (not shown) which is generally configured for acquiring and/or storing and/or forwarding medical data sets MED. The medical information system may, for example, have one or more databases (not shown). The databases may be implemented as local or distributed storage systems, for example as a PACS (picture archiving and communication system), a hospital information system (HIS), a laboratory information system (LIS), an "electronic medical record" (EMR) information system and/or as further medical information systems. According to some examples, the medical information system may also comprise one or more medical imaging modalities (not shown), such as for example a computed tomography system, a magnetic resonance system, an angiography system, a C-arm X-ray system, a positron emission tomography system, a mammography system, an X-ray system or the like.

The medical data set MED may include medical image data and/or other medical data not comprising any image data. In this context, image data may relate to medical image data with two or three spatial dimensions. The image data may additionally have a temporal dimension. The image data may for example have been produced with an imaging medical modality, such as for instance an X-ray, computed tomography, magnetic resonance, positron emission tomography or angiography machine or further equipment. Such image data may also be denoted radiology image data.

The medical data set PDS may furthermore also comprise histopathology image data in each case showing one or more histopathology images. Histopathology image data are image data which are based on a tissue sample from a patient. Tissue sections, which are stained with a histological stain, are dissected from the tissue sample. The tissue sections dissected in this manner are then digitized in order to obtain the histopathology image data. Specialized scanners, known as slide scanners, may be used for this purpose. The image captured in this way is also denoted a "whole slide image". The captured image data are typically two-dimensional pixel data.

The image data present in the medical data set PDS may, for example, be formatted in accordance with the DICOM format. DICOM (=digital imaging and communications in medicine) is an open standard for communicating and managing medical image data and associated data.

In addition to image data, the medical data set PDS may also comprise non-image data. Non-image data may for example be test results which are not based on medical imaging and may comprise laboratory data, vital data, spirometry data or records from neurological examinations. Non-image data may additionally comprise text data sets, such as for instance structured and unstructured medical investigation reports. Non-image data may furthermore also be patient-related data, such as for example demographic details relating to the patient, for instance relating to age, gender or body weight. The non-image data may for example be incorporated into the image data as metadata. Alternatively or additionally, the non-image data may for example also be saved in a patient electronic medical record (EMR), or in general separately from the image data. Such electronic medical records may for example be archived in the medical information system.

An analytical result RES for a medical data set MED can be ordered with a request REQ from the front-end computing device CLNT. The request REQ may for example to this end indicate the kind of desired analytical result RES, such as for instance the detection of possible lung lesions in medical image data of the lung. In addition, the request REQ may contain one or more constraints for the provision of the analytical result RES, such as a required quality or a required timeframe.

The analytical result RES may generally be an output produced by processing of the medical data set MED. In particular, the analytical result RES may be based on a diagnostic question or the analytical result may include an item of information relevant to the medical diagnosis. In particular, an analytical result RES is the output of a corresponding ML algorithm. One example of such an analytical result RES are pathological changes identified in image data of the medical data set MED, such as for instance lesions in radiology image data or tumor tissue in histopathology image data. Further examples of analytical results RES comprise values extracted from non-image data, such as anomalous vital or laboratory values.

The back-end computing device BKND may be implemented as a cloud or edge device. In the case of implementation as a cloud device, the back-end computing device BKND may be configured as a central computing device which, when required, promptly provides shared computer resources at low cost, usually via the internet and device-independently. In the event of implementation as an edge device, the back-end computing device BKND may be configured as a distributed computing device at the edge of the network of the client computing device CLNT and in particular of the medical information system. The back-end computing device BKND may be implemented as an individual component or include a group of computers, such as for instance a cluster. Such a system may also be known as a server system. The back-end computing device BKND is configured, for example by computer-readable instructions, by design and/or hardware, such that it can carry out one or more method steps according to some embodiments of the present invention.

The back-end computing device BKND may be connected via the interface INT to the front-end computing device CLNT. The back-end computing device BKND can receive via this interface INT medical data sets MED, P-MED and/or requests REQ, on the basis of which analytical results RES can be provided.

In order to provide analytical results RES, the processing unit VE of the back-end computing device 200 may have various modules STR, RUN, PRE and access an algorithm repository unit ALG-REP.

The algorithm repository unit ALG-REP may be configured as a centralized or distributed database. The algorithm repository unit ALG-REP may in particular be part of a server system. The algorithm repository unit ALG-REP is configured to store a number of different ML algorithms ALG1 . . . ALGN and keep them available for use. The ML algorithms ALG1 . . . ALGN may differ in that they in each case provide different kinds of analytical results RES. While one ML algorithm ALG1 is for example configured to automatically identify lung lesions in medical image data MED of the lung, another ML algorithm ALG2 may for example be configured to identify tumor cells in histopathology images, etc. In other words, the algorithm repository unit ALG-REP provides a kind of "library" of ML algorithms ALG1 . . . ALGN for providing different kinds of analytical results RES.

Figure 2:
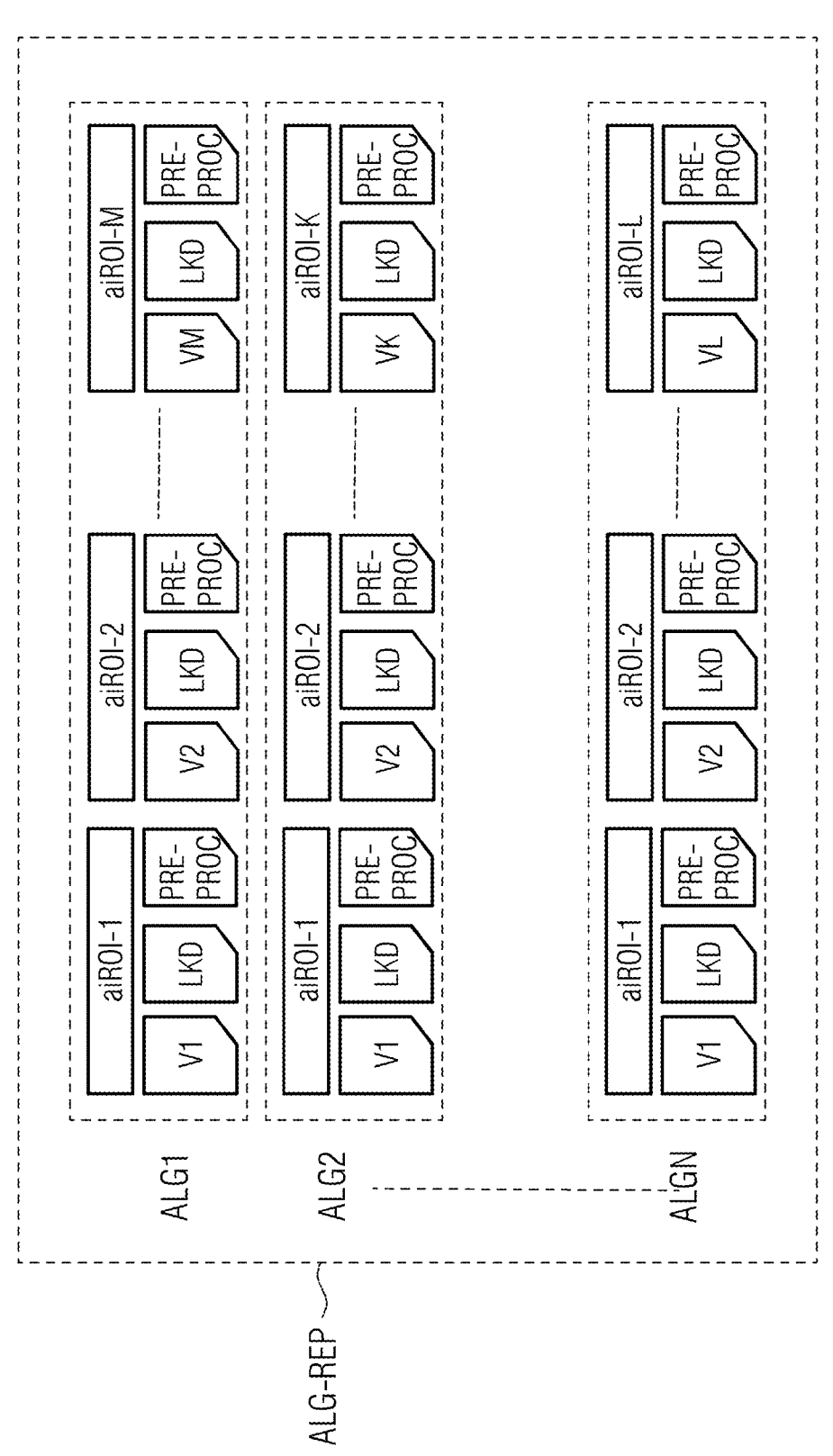
FIG. 2 shows a schematic representation of a data structure of an algorithm repository unit according to one embodiment.

The algorithm repository unit ALG-REP furthermore stores, as represented in the data storage structure shown in FIG. 2, different versions V1 . . . VM, which are optimized for different requests REQ and system statuses STA, of each ML algorithm ALG1 . . . ALGN. While the different versions V1 . . . VM of an ML algorithm ALG1 do yield the same kind of analytical result RES, they may differ in terms of quality, computational effort, resource requirements etc. A kind of "load balancing" in the system SYS may thus be achieved by selecting a specific version V1 . . . VM, for example by consciously accepting (still tolerable) quality losses in the case of a version V1 . . . VM in order to save computing power.

The inventors have identified and made use of the fact that an ML algorithm ALG1 . . . ALGN can be divided into versions V1 . . . VM by way of different types of preprocessing PRE-PROC of the medical data MED. Preprocessing PRE-PROC often determines both the resource consumption in the provision of an analytical result RES and its quality. Accordingly, the performance of an ML algorithm ALG1 . . . ALGN in identifying lesions in a specific organ may for example be improved by image enhancement and/or appropriate organ segmentation. Conversely, these preprocessing steps PRE-PROC may entail higher consumption of resources.

For example, the same lesions in a bronchial branch can be found with different versions V1 . . . VM but using fewer resources, because for example, as a result of preprocessing PRE-PROC (e.g. in the form of segmentation) of the underlying lung scans, only the bronchial branch is sent to the ML algorithm ALG1 (which is then faster but still finds the same lesions using fewer resources).

The ML algorithms ALG1 . . . ALGN are machine learning algorithms. The different versions V1 . . . VM of an ML algorithm ALG1 may thus be produced by the ML algorithm ALG1 having been trained using different types of preprocessing PRE-PROC. If there are, for example, N versions V1 . . . VM, they may have been produced by N different training steps of the base ML algorithm ALG1 on the basis of N different types of preprocessing PRE-PROC.

In order to identify a suitable version V1 . . . VM for the respective system status STA and respective request REQ, the algorithm repository unit ALG-REP stores an area of application aiROI for each version V1 . . . VM. The area of application aiROI may for example indicate the preprocessing PRE-PROC to be carried out for the respective version and the performance characteristics LKD of the respective version. The performance characteristics LKD may here, for example, be a quality level and/or a resource requirement. If, for example, the medical data sets MED contain image data, the area of application aiROI may additionally comprise an imaging protocol which corresponds to the image data, on the basis of which the respective version V1 . . . VM was trained.

The computing modules STR, RUN, PRE of the processing unit VE may be configured as virtual or real machines. According to one embodiment, the computing modules STR, RUN, PRE are implemented as Kubernetes nodes.

The computing module STR may here be configured as a control module or control node. The control module STR may in particular be configured as the Kubernetes "master" node which controls the functions and processes of processing, distributes work orders and requests resources for example in the form of Kubernetes "worker" nodes.

The computing module RUN may be provided as a node for executing the corresponding versions V1 . . . VM of the ML algorithm ALG1 . . . ALGN. The computing module RUN may be configured as a Kubernetes worker node in which individual versions V1 . . . VM are hosted in Kubernetes pods and applied.

The computing module PRE may be configured as a node for carrying out appropriate preprocessing PRE-PROC for producing preprocessed medical data sets P-MED. The computing module PRE may be configured as a Kubernetes worker node in which individual preprocessing processes PRE-PROC are hosted in Kubernetes pods.

The control module STR is configured to process the request REQ and optionally request an item of status information STA (or system status STA) from the system SYS. The status information STA may generally relate to a level of utilization of the system SYS and for example indicate how heavily utilized are the computing capacities of the back-end computing device BKND and/or of the front-end computing device CLNT or corresponding data transmission capacities. Processing of the request REQ may involve defining a kind of desired analytical result RES and certain performance limit values which must be complied with for provision of the analytical result RES. The performance limit values may for example relate to a quality level of the analytical result RES or a time interval for provision of the analytical result RES. The control module STR is furthermore configured in principle firstly to select, on the basis of the request REQ and/or on the basis of the medical data set MED, a type of required ML algorithm ALG1 . . . ALGN from the algorithm repository unit ALG-REP. The control module STR is furthermore configured then to select, on the basis of the request REQ and/or the medical data set MED and/or the status information STA and/or the performance characteristics LKD and/or the performance limit values, a suitable area of application aiROI for the selected ML algorithm ALG1 . . . ALGN and thus a version V1 . . . VM of the selected ML algorithm ALG1 . . . ALGN.

The selected area of application aiROI is accompanied by preprocessing PRE-PROC which has to be implemented. The control module STR is to this end configured to request corresponding preprocessing PRE-PROC and optionally provide corresponding means, mechanism and/or functionality, either within the processing unit VE, i.e. in the computing module PRE, or outside the processing unit VE, for example in the front-end computing device CLNT. The control module STR is furthermore configured to request application of the selected version V1 . . . VM to the preprocessed medical data set P-MED, for example in the computing module RUN.

The subdivision undertaken of the processing unit VE into modules STR, RUN, PRE here serves merely to simplify the explanation of the functionality of the back-end computing device BKND and should not be understood limitingly. The modules STR, RUN, PRE or the functions thereof may also be combined into one element. The modules STR, RUN, PRE may here in particular also be understood as computer program products or computer program segments which, on execution in the back-end computing device BKND, implement one or more of the method steps described herein.

The training computing device TRNG is configured to train (adapt) an ML algorithm ALG1 . . . ALGN on the basis of suitable training data. The training computing device TRNG is furthermore configured to provide ML algorithms ALG1 . . . ALGN trained (adapted) in this way as versions V1 . . . VM and associated areas of application aiROI according to the embodiments described herein. The training computing device TRNG may comprise a processor, an interface and a repository unit (which may, for example, be configured in a computer). The processor controls the training computing device TRNG by executing computer program instructions, the method steps shown in FIG. 6 possibly being defined by the computer program instructions. The repository unit may serve as an archive for the training data sets described herein. The interface may in particular be configured to establish a data link between the training computing device TRNG and back-end computing device BKND.

Figure 3:
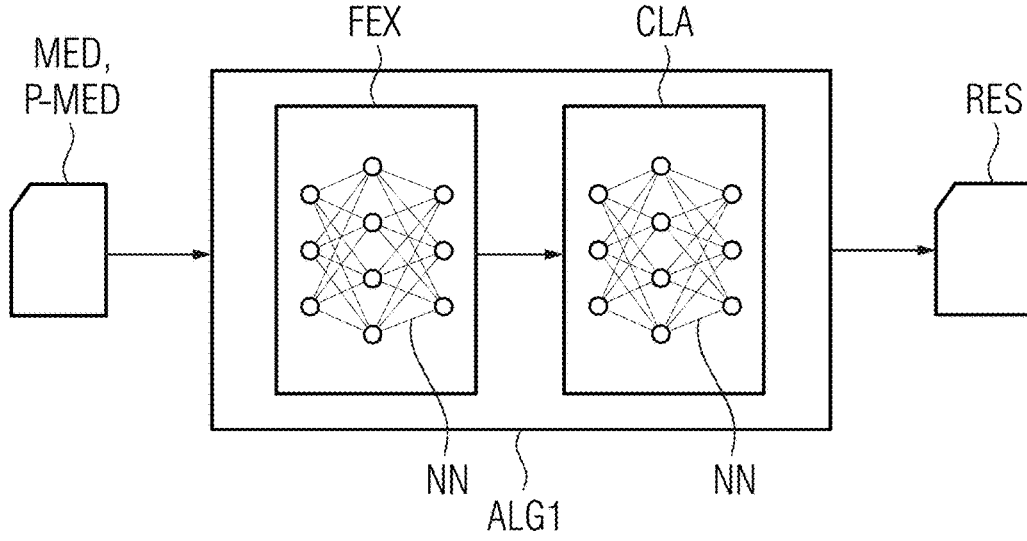
FIG. 3 shows a schematic representation of an ML algorithm according to one embodiment.

The most varied ML algorithms ALG1 . . . ALGN are conceivable which are suitable or have been trained for processing a medical data set MED or a preprocessed medical data set P-MED in order to provide a diagnostic analytical result RES. By way of example, FIG. 3 shows one possible implementation of an ML algorithm ALG1 according to one embodiment.

The ML algorithm ALG1 according to this embodiment is trained to automatically detect medical anomalies in medical image data and in particular lesions in captures of a patient's lung. Without any condition of generality, the ML algorithm ALG1 comprises two trained components FEX, CLA which interact for image data analysis and classification. The component FEX may here be configured to identify possible candidates for lesions in the image data MED with sufficient sensitivity. The component CLA may be configured to classify the candidates into actual lesions and "false positive" candidates with sufficient specificity.

Such trained functions FEX, CAS may generally include intelligent algorithms or computer program products which are suitable for identifying patterns and classifying them according to a learned task. This definition comprises any suitable data mining tools and techniques, such as support vector machines, decision trees, naive Bayes or neural networks.

In particular, according to one implementation, the algorithm ALG1 may comprise one or more neural networks NN. A neural network NN is defined in the form of a plurality of sequential layers. A first group of neural network layers FEX may be applied in order to preprocess the image data in the course of preprocessing PRE-PROC and then extract features or patterns from the input data MED. The features extracted in this way may be understood as candidates for medical anomalies such as for example lung lesions. These candidates may be supplied as input values to a second group of network layers, also known as classifier CLA. The classifier serves to classify the candidates into actual anomalies and incorrectly identified anomalies. The actually identified anomalies can then be provided as the analytical result RES.

The neural networks NN of the two components FEX and CLA may use various kinds of networks and layers, such as for example convolutional layers, pooling layers (e.g. max pooling or average pooling layers), upsampling layers, deconvolutional layers and fully connected layers or other types of layers. Convolutional layers convolve the input and forward their result to the next layer by moving an image filter kernel over the input. Pooling layers reduce the dimensions of the data by combining the outputs of clusters of network nodes of a layer into a single network node on the next layer. Upsampling and deconvolutional layers reverse the actions of the convolutional and pooling layers. A fully connected layer connects each network node in a layer with each network node in another layer such that substantially each result is processed in the immediately next layer. According to one implementation, it is, however, also possible to use skip or jump connections such that layers can be bypassed. Such a configuration is also denoted a ResNet and enables training of deeper networks.

In general, ML algorithm ALG1 learns this embodiment by adapting weights or weighting parameters of individual layers and network nodes on the basis of training data. Instead of "preprogramming" potential indicators for analytical results RES, such as image patterns of lesions, the architecture of the ML algorithm ALG1 may be adapted in order to learn these indicators at different levels of abstraction on the basis of input data MED. The ML algorithm ALG1 may preferably be trained using a supervised learning method. A well established method is "backpropagation", which can be applied for embodiments of the present invention. During training, the ML algorithm ALG1 is applied to training input values (i.e. medical training data sets) in order to produce corresponding intermediate analytical results RES whose target values are known ("verified" analytical results). The difference between intermediate and verified analytical results (e.g. in the form of the mean squared error difference between intermediate and verified analytical results) may be used in order to introduce a cost or loss function as a measure of how well or badly the ML algorithm ALG1 is operating. The objective of training is to find a (local) minimum of the loss function by iteratively adapting the weights of the ML algorithm ALG1 in such a way that the ML algorithm ALG1 is ultimately enabled to produce acceptable results over a (sufficiently) large cohort of training data. This optimization problem can be carried out using a stochastic gradient method or other approaches known in the art. In principle, an ML algorithm ALG1 comprising one or more components FEX, CLA can be trained by adapting either the candidate generation FEX branch or the candidate classification CLA branch or both. For example, the candidate generation FEX branch may be adapted such that, from the outset, meaningful candidates are extracted and/or as far as possible all lesions are detected. The candidate classification CLA branch may furthermore be trained such that a suitable classification scheme is learned and/or applied in order to eliminate as many false positive candidates as possible.

The various versions V1 . . . VM of the ML algorithm may differ not only by having different weights in the network layers but also by having different network architectures with different kinds and numbers of layers. The different versions V1 . . . VM may be provided in that the ML algorithm is in each case trained on the basis of medical data MED preprocessed with different types of preprocessing PRE-PROC.

According to some embodiments of the present invention, preprocessing PRE-PROC may also take place in the ML algorithm ALG1 itself. In this way, individual network layers can be associated with a type of preprocessing PRE-PROC. For example, a convolution (which always proceeds identically) of the input data may be considered to be preprocessing PRE-PROC. This preprocessing PRE-PROC (and the network layers associated therewith) may for example be split off from the ML algorithm ALG1 in order to produce a version V1 . . . VM. In order to provide such preprocessing PRE-PROC separately from the respective version V1 . . . VM, a corresponding computer program product may be provided as "means" for carrying out the corresponding preprocessing PRE-PROC in the system SYS. In other words, processing steps or network layers split off from the ML algorithm ALG1 on creation of a version V1 . . . VM may accordingly be carried out separately from application of the "remainder" of the ML algorithm ALG1, so creating additional flexibility in the system SYS.

Figure 4:
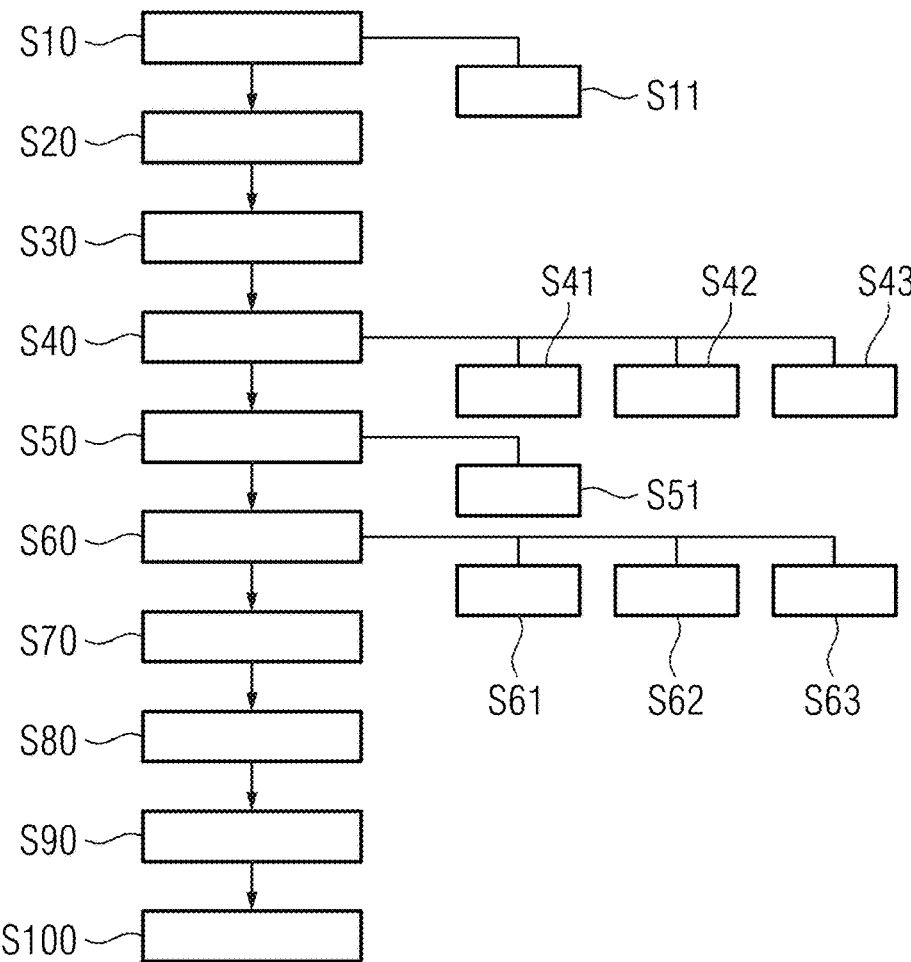
FIG. 4 shows a sequence diagram of a method for providing an analytical result according to one embodiment.

FIG. 4 shows a schematic sequence diagram of a method for providing an analytical result RES. The order of the method steps is not limited either by the sequence shown or by the selected numbering. Accordingly, the order of the steps may optionally be interchanged and individual steps may be omitted. Moreover, one or more steps, in particular a sequence of steps, and optionally the entire method may be carried out repeatedly. According to some embodiments of the present invention, the following steps may be carried out entirely or in part by the processing unit VE or in particular by the control module STR.

In step S10, a request REQ is transmitted from the front-end computing device CLNT and received via the interface INT in the back-end computing device BKND. The request REQ is directed toward creating a specific (or specific by type) analytical result RES on the basis of a specific medical data set MED. The medical data set MED is here at the disposal of the front-end computing device CLNT. The request REQ may furthermore directly or indirectly specify specific general conditions for the provision of the analytical result RES by the back-end computing device BKND, such as for instance a quality level (e.g. in terms of a confidence, sensitivity and/or specificity level) or a timeframe. In an optional step S11, the medical data set MED is furthermore provided by the front-end computing device CLNT via the interface INT to the back-end computing device BKND.

In step S20, the above-described algorithm repository unit ALG-REP is provided. This may in particular mean that the processing unit VE within the back-end computing device can access the algorithm repository unit ALG-REP in order to select an ML algorithm ALG1 . . . ALGN and compare the various areas of application aiROI with the request REQ.

In step S30, the type of ML algorithm ALG1 . . . ALGN which is to be applied to the medical data set MED for the kind of analytical result RES to be produced is firstly generally selected.

In step S40, an area of application aiROI for the selected ML algorithm ALG1 and thus the version V1 . . . VM of the ML algorithm which is to be used are selected. In an optional substep S41, the system status STA of the system SYS may firstly be detected for this purpose. In an optional substep S42, a suitable area of application aiROI can be selected on the basis of performance characteristics LKD of the particular version V1 . . . VM in each case present in the areas of application aiROI, on the basis of general conditions present in the request REQ and/or of the system status STA, which selected suitable area of application aiROI on the one hand fulfills the general conditions and on the other hand is coordinated with the available system resources or the system status STA. According to some embodiments, an optimization problem may to this end be formulated in step S42, in which for example individual parameters enter into a cost function which is to be minimized. If the medical data set MED to be analyzed comprises image data, an area of application aiROI can furthermore be identified on the basis of the imaging protocol with which the image data was captured. To this end, the imaging protocol can be identified in an optional step S43 and taken into account on selection of the area of application aiROI.

Since each area of application aiROI is associated with a specific type of preprocessing PRE-PROC and a specific version V1 . . . VM of the ML algorithm, it is possible in step S50 to identify the preprocessing PRE-PROC to be carried out and/or (in the optional substep S51) the version V1 . . . VM to be applied.

In step S60, the preprocessing PRE-PROC to be carried out can be requested on this basis. Depending on system status STA, this may proceed in the front-end computing device CLNT or the back-end computing device CLNT. To this end, provision may be made in an optional substep S61 for an evaluation to be carried out on the basis of the system status STA as to whether the preprocessing PRE-PROC is to be performed by the front-end computing device CLNT (or by the network into which the front-end computing device CLNT is integrated) or the back-end computing device BKND (e.g. in a preprocessing computing module PRE). If the preprocessing PRE-PROC is to be carried out by the front-end computing device CLNT, provision may be made in step S62 for the back-end computing device BKND to provide the front-end computing device CLNT with means, mechanism and/or functionality for carrying out the preprocessing PRE-PROC. These means, mechanism and/or functionality may for example in particular comprise executable computer program products which are configured to carry out the respective preprocessing PRE-PROC. In an optional step S63, the preprocessed medical data set P-MED can then be received from the front-end computing device CLNT via the interface INT in the back-end computing device BKND.

In step S70, computing resources for applying the selected version V1 . . . VM to the preprocessed medical data set P-MED can then be requested. For example, resources in the computing module RUN may be allocated for this purpose.

In step S80, the selected version V1 . . . VM is applied by the requested resource within the back-end computing device BKND to the preprocessed medical data set P-MED. In this way, the analytical result RES is provided. The analytical result RES may be provided to the front-end computing device CLNT via the interface INT.

In an optional step S90, the analytical result RES may be evaluated. This may proceed either automatically by the back-end computing device BKND or on the basis of feedback from a user on the front-end computing device CLNT. For example, a confidence level of the analytical result RES may be evaluated, or it can be evaluated whether for example incorrectly identified lesions have been discarded or non-identified lesions have been added.

In an optional step S100, the ML algorithm ALG1 . . . ALGN can be retrained on the basis of step S90. In particular, on the basis of the evaluation, a new version V1 . . . VM of the ML algorithm ALG1 . . . ALGN and an associated area of application aiROI may be produced and stored in the algorithm repository unit ALG-REP.

Figure 5:
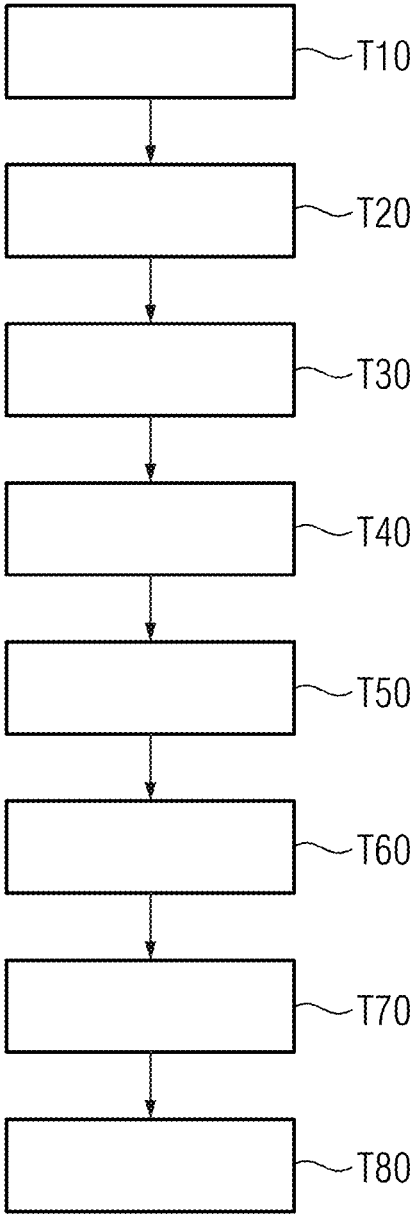
FIG. 5 shows a sequence diagram of a method for providing an area of application.

FIG. 5 shows an exemplary development of a computer-implemented method for providing an analysis function AF comprising a trained function. The order of the method steps is not limited either by the sequence shown or by the selected numbering. Accordingly, the order of the steps may optionally be interchanged and individual steps may be omitted. Moreover, one or more steps, in particular a sequence of steps, and optionally the entire method may be carried out repeatedly.

In step T10, an ML algorithm ALG1 . . . ALGN or a version V1 . . . VM of the ML algorithm ALG1 . . . ALGN is provided. The ML algorithm ALG1 . . . ALGN, or the version V1 . . . VM, may here be pretrained, i.e. one or more parameters have already been adapted by the described training method and/or another training method. Alternatively, one or more parameters may not yet have been adapted by way of training data, in particular one or more parameters may have a preassigned constant value and/or random value.

In step T20, at least one medical training data set MED and an associated verified analytical result RES are provided. The training data set or sets MED may here in principle have the same form as the medical data sets MED. Verified analytical results may for example be based on annotation by an expert or user.

In step T30, a defined type of preprocessing PRE-PROC is applied to the training data set or sets MED. The preprocessing PRE-PROC may for example be predetermined and fulfill specific characteristics with regard to quality or resource consumption on subsequent use in the system SYS. According to other examples, the preprocessing PRE-PROC may itself be based on training or comprise a trained function.

In step T40, the ML algorithm ALG1 . . . ALGN is applied to the preprocessed training data set or sets P-MED in order to produce an "intermediate" analytical result. The intermediate analytical results here correspond to a prediction of the associated verified analytical result RES.

In step T50, the intermediate analytical results are compared with the associated verified analytical results RES, whereupon the ML algorithm ALG1 . . . ALGN is adapted on the basis of the comparison in step T60. This may, for example, proceed on the basis of a loss function which punishes incorrectly selected analytical results. In particular, one or more parameters of the ML algorithm ALG1 . . . ALGN may be adapted such that the loss function is minimized, for example by backpropagation. In order to minimize the loss function, the comparison is carried out for various paired sets of intermediate and verified analytical results until a local minimum of the loss function is achieved and the version V1 . . . VM of the ML algorithm ALG1 . .

. ALGN is operating satisfactorily. The ML algorithm ALG1 . . . ALGN adapted in this way is finally provided.

In step T70, on the basis of the adapted ML algorithm ALG1 . . . ALGN or on the adaptation process in step T60, an area of application aiROI is created which includes the performance characteristics LKD of the adapted ML algorithm ALG1 . . . ALGN and the underlying preprocessing PRE-PROC.

In step T80, the adapted ML algorithm ALG1 . . . ALGN is finally stored in the algorithm repository unit ALG-REP as a new version V1 . . . VM of the ML algorithm ALG1 . . . ALGN together with the associated area of application aiROI.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

While exemplary embodiments have been described in detail in particular with reference to the figures, it should be noted that numerous modifications are possible. It should moreover be noted that the exemplary embodiments are merely examples which are not in any way intended to limit the scope of protection, application and structure. Instead, the preceding description provides a person skilled in the art with guidance for implementing at least one exemplary embodiment, it being possible for various modifications, in particular alternative or additional features and/or modification of the function and/or arrangement of the described components, to be made as desired by a person skilled in the art without in so doing deviating from the subject matter in each case defined in the appended claims and its legal equivalent and/or departing from the scope of protection thereof.

What is claimed is:

1. A computing device to provide an analytical result based on an evaluation of a medical data set, the computing device comprising:
an interface linked, for data purposes, to a second computing device, the interface configured to
receive medical data sets and a request to provide an analytical result of the medical data set from the second computing device, and
provide the analytical result to the second computing device;
a memory including an algorithm repository and computer readable instructions, the algorithm repository including
at least one ML algorithm trained to provide an analytical result based on medical data sets, and
for each ML algorithm, a plurality of areas of application, each area of application of an ML algorithm corresponding to a different type of preprocessing of the medical data set prior to application of the ML algorithm; and
at least one processor configured to execute the computer readable instructions to cause the computing device to
select an ML algorithm from the memory based on the request,
acquire an item of status information of at least one of the computing device, the second computing device, or a data transmission between the computing device and the second computing device,
select an area of application for the selected ML algorithm based on the item of status information and at least one of the request or the medical data set,
request preprocessing of the medical data set in accordance with a respective preprocessing associated with the selected area of application to provide a preprocessed medical data set, and
apply the selected ML algorithm to the preprocessed medical data set to provide the analytical result.

2. The computing device as claimed in claim 1, wherein the algorithm repository has a different version of the ML algorithm for each respective area of application of the ML algorithm, each different version is specific to the respective area of application,
the at least one processor is configured to cause the computing device to select the version of the ML algorithm which corresponds to the selected area of application, and
the at least one processor is configured to cause the computing device, on application of the ML algorithm, to apply the selected version of the ML algorithm to the preprocessed medical data set to provide the analytical result.

3. The computing device as claimed in claim 1, wherein the plurality of areas of application in each case include performance characteristics of the ML algorithm during the respective preprocessing, and
the at least one processor is configured to cause the computing device to select the area of application additionally based on the performance characteristics.

4. The computing device as claimed in claim 3, wherein the performance characteristics include at least one of an item of information characterizing a quality of the analytical result or an item of information characterizing a consumption of resources on application of the selected ML algorithm for the respective preprocessing.

5. The computing device as claimed in claim 4, wherein the at least one processor is configured to cause the computing device to select the area of application based on the performance characteristics to optimize at least one of the quality of the analytical result to be provided or the consumption of resources for provision of the analytical result.

6. The computing device as claimed in claim 1, wherein the at least one processor is configured to cause the computing device to
determine, based on at least one of the status information or the selected area of application, whether the preprocessed data set is to be requested from the second computing device or a resource within the computing device, and
request, as a function of the determination, the preprocessed data set from the second computing device or from the resource within the computing device.

7. The computing device as claimed in claim 1, wherein the at least one processor is configured to cause the computing device to request the preprocessed medical data set from the second computing device, and enable the second computing device to provide the preprocessed data set.

8. The computing device as claimed in claim 1, wherein the at least one ML algorithm has, in each case, been trained by carrying out, in each case, at least one training step using the types of preprocessing corresponding to the plurality of areas of application.

9. The computing device as claimed in claim 1, wherein the medical data set includes medical image data, the analytical result is based on detection of medical anomalies in the medical image data, and the preprocessing includes segmentation of the medical image data.

10. The computing device as claimed in claim 9, wherein the medical image data is generated based on an imaging protocol, the imaging protocol is associated with at least one area of application, and the at least one processor is configured to cause the computing device to acquire the imaging protocol of the medical image data, and select the area of application additionally based on the acquired imaging protocol and the associated at least one area of application.

11. The computing device as claimed in claim 1, further comprising:

a training computing device configured to carry out an evaluation of the provided analytical result, and based on the evaluation, adapt at least one of the area of application or the ML algorithm by further training of the ML algorithm.

12. The computing device as claimed in claim 1, wherein the computing device is at least in part configured as at least one of an edge or cloud device.

13. A computer-implemented method for providing an analytical result by evaluating a medical data set with a computing device, the computer-implemented method comprising:

receiving a request to provide an analytical result of the medical data set from a second computing device;

providing, in the computing device, an algorithm repository unit-having at least one ML algorithm trained to provide analytical results based on medical data sets, and for each ML algorithm, a plurality of areas of application, each area of application of an ML algorithm corresponding to a different type of preprocessing of the medical data set prior to application of the ML algorithm;

selecting an ML algorithm from the algorithm repository based on the request;

acquiring an item of status information of at least one of the computing device, the second computing device, or a data transmission between the computing device and the second computing device selecting an area of application based on the item of status information and at least one of the request or the medical data set;

requesting preprocessing corresponding to the preprocessing associated with the selected area of application to provide a preprocessed data set; and applying the ML algorithm to the preprocessed medical data set to provide the analytical result to the second computing device.

14. The computing device as claimed in claim 1, wherein the medical data set includes medical image data, the analytical result is based on detection of medical anomalies in the medical image data, and the preprocessing includes preprocessing of the medical image data.

15. A non-transitory computer-readable storage medium storing computer-executable program instructions that, when executed at a computing device, cause the computing device to perform the method of claim 13.

16. A computing device to provide an analytical result based on detection of medical anomalies in medical image data of a medical data set, the medical image data generated based on an imaging protocol, the computing device comprising:

an interface linked, for data purposes, to a second computing device, the interface configured to receive medical data sets and a request to provide an analytical result of the medical data set from the second computing device, and provide the analytical result to the second computing device;

a memory including an algorithm repository and computer readable instructions, the algorithm repository including at least one ML algorithm trained to provide an analytical result based on medical data sets, and for each ML algorithm, a plurality of areas of application, each area of application of an ML algorithm corresponding to a different type of preprocessing of the medical data set prior to application of the ML algorithm, and the imaging protocol associated with at least one area of application; and at least one processor configured to execute the computer readable instructions to cause the computing device to select an ML algorithm from the memory based on the request, acquire the imaging protocol of the medical image data, select an area of application for the selected ML algorithm based on the acquired imaging protocol and at least one of the request or the medical data set, request preprocessing of the medical data set in accordance with a respective preprocessing associated with the selected area of application to provide a preprocessed data set, the preprocessing including segmentation of the medical imaging data, and apply the selected ML algorithm to the preprocessed medical data set to provide the analytical result.

* * * * *